US012758673B2

(12) United States Patent
Kawanishi et al.

(10) Patent No.: US 12,758,673 B2
(45) Date of Patent: Oct. 13, 2026

(54) ODOR PRESENTATION MODULE, ODOR PRESENTATION DEVICE, AND ODOR PRESENTATION METHOD

(71) Applicant: Sony Group Corporation, Tokyo (JP)

(72) Inventors: Mitsuhiro Kawanishi, Tokyo (JP); Kazuhiko Miyahara, Tokyo (JP); Yoshio Goto, Tokyo (JP)

(73) Assignee: Sony Group Corporation, Tokyo (JP)

( * ) Notice: Subject to any disclaimer, the term of this patent is extended or adjusted under 35 U.S.C. 154(b) by 387 days.

(21) Appl. No.: 18/563,190

(22) PCT Filed: Mar. 18, 2022

(86) PCT No.: PCT/JP2022/012562
§ 371 (c)(1),
(2) Date: Nov. 21, 2023

(87) PCT Pub. No.: WO2022/254884
PCT Pub. Date: Dec. 8, 2022

(65) Prior Publication Data
US 2024/0374776 A1 Nov. 14, 2024

(30) Foreign Application Priority Data
May 31, 2021 (JP) ................................ 2021-091083

(51) Int. Cl.
*A61L 9/12* (2006.01)

(52) U.S. Cl.
CPC ......... *A61L 9/125* (2013.01); *A61L 2209/134* (2013.01)

(58) Field of Classification Search
CPC .... A61L 9/125; A61L 2209/134; F24F 1/008; F24F 8/50; G09F 19/005; A61M 2021/0016
See application file for complete search history.

(56) References Cited

U.S. PATENT DOCUMENTS 4,633,533 A * 1/1987 Meehan .................... A61L 9/12 4/222
2012/0091231 A1* 4/2012 Ajagbe .................... A61L 9/05 239/418
(Continued)

FOREIGN PATENT DOCUMENTS

CN 209210122 U * 8/2019
JP H07155956 A 6/1995
(Continued)

OTHER PUBLICATIONS

International Search Report from corresponding PCT application PCT/JP2022/012562, dated May 17, 2022.

*Primary Examiner* — Jennifer Wecker
*Assistant Examiner* — Brady C Pilsbury
(74) *Attorney, Agent, or Firm* — K&L Gates LLP

(57) ABSTRACT

To provide an odor presentation module capable of discharging an odor-containing airflow over a wide area.
An odor presentation module 100 includes a first opening portion 104 that emits a first airflow containing an odor, a second opening portion 113 that emits a second airflow, and a retention nozzle 110 having a retention space in which the first airflow and the second airflow are retained, wherein a direction of the first airflow emitted from the first opening portion 104 is controlled by the second airflow. The odor presentation module 100 has the retention nozzle 110 capable of being attached to and detached from the second opening portion 113 and having a plurality of discharge holes 133, and further includes a first airflow generation device 101 and an odor carrying portion 103 that carries an odor, wherein the first airflow can be formed by mixing an airflow generated by the first airflow generation device 101 and the odor carried by the odor carrying portion 103.

14 Claims, 7 Drawing Sheets

(56) References Cited

U.S. PATENT DOCUMENTS

| | | | |
|---|---|---|---|
| 2018/0147484 A1 | 5/2018 | Osawa et al. | |
| 2019/0262739 A1* | 8/2019 | Reichow | A63J 5/00 |
| 2021/0199104 A1 | 7/2021 | Kim et al. | |
| 2021/0206162 A1* | 7/2021 | Bishop | B41J 2/04501 |
| 2022/0143254 A1 | 5/2022 | Inoue et al. | |

FOREIGN PATENT DOCUMENTS

| | | | |
|---|---|---|---|
| JP | 2010142669 | A | 7/2010 |
| JP | 2014092674 | A | 5/2014 |
| JP | 5652431 | B2 | 1/2015 |
| JP | 2019195442 | A | 11/2019 |
| JP | 2020162644 | A | 10/2020 |
| JP | 2021058427 | A | 4/2021 |
| WO | 2016/199441 | A1 | 12/2016 |
| WO | 2019/131808 | A1 | 7/2019 |
| WO | 2020/179256 | A1 | 9/2020 |

* cited by examiner

ODOR PRESENTATION MODULE, ODOR PRESENTATION DEVICE, AND ODOR PRESENTATION METHOD

TECHNICAL FIELD

The present technology relates to an odor presentation module, an odor presentation device, and an odor presentation method, and more particularly, to an odor presentation module, an odor presentation device, and an odor presentation method that control an odor presented to a user (user) by airflow.

BACKGROUND ART

Conventionally, a technology has been proposed to generate a fragrance gas in which liquid fragrance is vaporized, and to provide fragrance to a user by controlling the generated fragrance gas with a blower airflow.

For example, PTL 1 proposes a booster device for enhancing the ability of a fragrance display to inject fragrance, wherein the fragrance display includes a columnar shape having a first face, a second face, and sides, the first face being provided with an injection port to inject fragrance, and the fragrance display being provided with a wind source to inject the fragrance outside the fragrance display. The booster device includes a housing for accommodating the fragrance display inside and a fan provided inside the housing, the housing including a tubular outer housing having an air supply opening for taking in air, and further including a narrowing member that is provided at an end of the first side of the fragrance display and narrows the flow of air formed by the fan.

Also, PTL 2 proposes a humidifier that includes a main body having a ventilation pathway connecting an intake port and a discharge port for air, a humidifying means disposed in the ventilation pathway and supplied with water, a blowing fan disposed in the ventilation pathway to take air in through the intake port and discharge the air from the discharge port to the outside through the humidifying means, a water tank portion, and a water supply means for supplying water for humidification from the water tank portion to a humidifying element. When humidifying, the water for humidification is scooped up from the water tank portion by a water pump, and the hot water is discharged downward from a shower head toward the humidifying element, thereby absorbing moisture into the humidifying element, and dry air in the room that has been drawn in through the intake port by the rotation of the blowing fan is passed through the humidifying element, thereby humidification is performed.

CITATION LIST

Patent Literature

[PTL 1]
JP 2020-162644A
[PTL 2]
JP 5652431B

SUMMARY

Technical Problem

However, a problem in the technology of PTL 1 is that, since a nozzle is used to narrow the airflow, and the nozzle diameter is smaller than the fan, in this structure, the airflow is thin and must be pinpointed to the nose of the user, and if the face of the user moves, the nose moves away from the airflow and loses the smell.

The humidifier described in PTL 2 is characterized in using water, so there is no need to consider odor leakage or fragrance deposition, and the contact area between the liquid and gas can be configured in an open system, making it possible to increase the size. On the other hand, in the case of an odor presentation module that uses fragrance, if the contact area between the liquid and gas is an open system, fragrance will adhere to the device, causing odor leakage and fragrance deposition to become a problem. Therefore, the contact area between the liquid and gas must be a sealed system, and a fragrance gas discharge hole must be small. This creates the problem that the fragrance gas flow must be thin and wide.

Therefore, a main object of the present technology is to provide an odor presentation module capable of discharging an odor-containing airflow over a wide area.

Solution to Problem

The present technology provides an odor presentation module that includes a first opening portion that emits a first airflow containing an odor, a second opening portion that emits a second airflow, and a retention nozzle having a retention space in which the first airflow and the second airflow are retained, wherein a direction of the first airflow emitted from the first opening portion is controlled by the second airflow. In the odor presentation module, the retention nozzle can be attached to and detached from the second opening portion and can have a plurality of discharge holes, the odor presentation module further including a first airflow generation device, and an odor carrying portion for carrying the odor, wherein the first airflow is generated by a combination of the airflow generated by the first airflow generation device and the odor carried by the odor carrying portion.

The present technology also provides an odor presentation device that includes: a plurality of odor presentation modules having a first opening portion for emitting a first airflow containing an odor and second opening portions for emitting a second airflow, a direction of the first airflow emitted from the first opening portion being controlled by the second airflow; and a retention nozzle that has a retention space in which the first airflow and the second airflow emitted from the plurality of odor presentation modules are integrated and retained, and that can be attached to and detached from each of the second opening portions.

The present technology also provides an odor presentation method that includes the steps of emitting a first airflow containing an odor, emitting a second airflow, and retaining the first airflow and the second airflow in a retention space, wherein a direction of the first airflow emitted from the first opening portion is controlled by the second airflow.

Advantageous Effects of Invention

According to the present technology, an odor presentation module capable of discharging an odor-containing airflow over a wide area can be provided. The foregoing effect is not necessarily limited, and any effect described in the present specification or other effects achievable from the present specification may be obtained in addition to the foregoing effect or instead of the foregoing effect.

DESCRIPTION OF EMBODIMENTS

Hereinafter, preferable embodiments for implementing the present technology will be described with reference to the drawings. The embodiments which will be described later illustrate examples of representative embodiments of the present technology, and any of the embodiments can be combined. The scope of the present technology is not to be construed narrowly by these. The explanations are given in the following order.

1. First Embodiment
(1) Configuration Example of Odor Presentation Module
(2) Configuration Example of Retention Nozzle
(3) Operation Example of Odor Presentation Module (Odor Presentation Method)
2. Second Embodiment
(1) Configuration Example of Odor Presentation Module
(2) Operation Example of Shutter Mechanism
3. Third Embodiment
(1) Configuration Example of Odor Presentation Module
(2) Operation Example of Shutter Mechanism
4. Fourth Embodiment
(1) Configuration Example of Odor Presentation Module
(2) Operation Example of Shutter Mechanism
5. Fifth Embodiment
(1) Configuration Example of Odor Presentation Module
(2) Operation Example of Shutter Mechanism
6. Sixth Embodiment
(1) Configuration Example of Odor Presentation Module
(2) Operation Example of Shutter Mechanism
7. Seventh Embodiment
(1) Configuration Example of Odor Presentation Device
(2) Configuration Example of Odor Presentation Portion
(3) Configuration Example of Variable Mechanism

1. First Embodiment (1) Configuration Example of Odor Presentation Module

Figure 1:
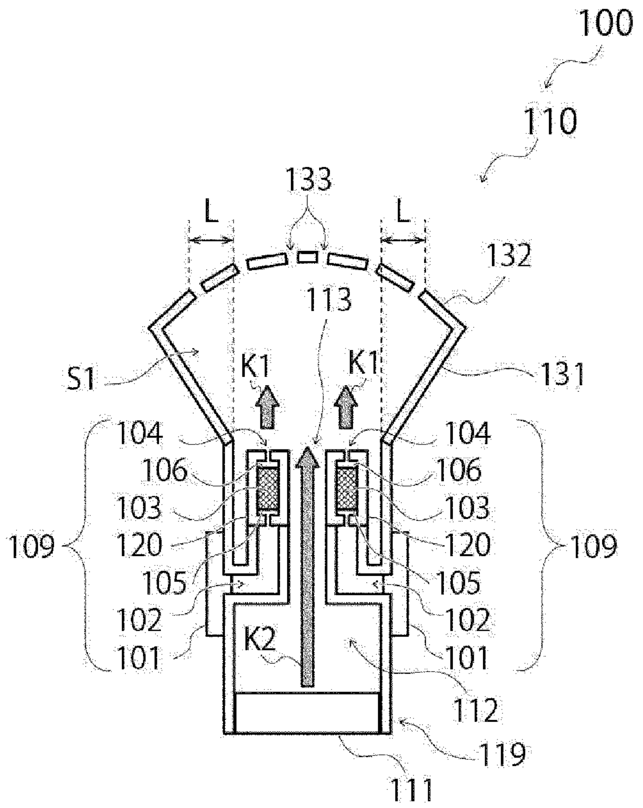
FIG. 1 is a schematic side view showing a configuration example of an odor presentation module according to a first embodiment of the present technology.
Figure 2:
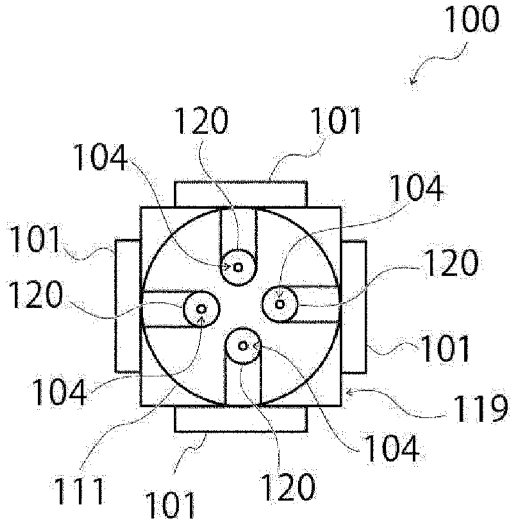
FIG. 2 is a schematic plan view showing a configuration example of the odor presentation module according to the first embodiment of the present technology.

A configuration example of an odor presentation module 100 according to a first embodiment of the present technology will be described with reference to FIG. 1 and FIG. 2. FIG. 1 is a schematic side view showing a configuration example of the odor presentation module 100 according to the present embodiment. FIG. 2 is a schematic plan view showing a configuration example of the odor presentation module 100.

As shown in FIG. 1, the odor presentation module 100 according to the present embodiment includes an odor-containing airflow generation portion 109, a control airflow generation portion 119 that controls an odor-containing airflow generated by the odor-containing airflow generation portion 109, and a retention nozzle 110 that temporarily retains airflows emitted from the odor-containing airflow generation portion 109 and the control airflow generation portion 119. Note that there may be provided only one odor-containing airflow generation portion 109, or two or more of it may be provided.

The odor-containing airflow generation portion 109 includes a first airflow generation device 101 such as a micro blower, a first flow path 102 provided with the first airflow generation device 101 at one end, an odor carrying portion 103 provided in the first flow path 102, and a first opening portion 104 which is the other end of the first flow path 102. The odor-containing airflow generation portion 109 generates an odor-containing first airflow (odor-containing airflow) K1 by having the components described above.

The control airflow generation portion 119 includes a second airflow generation device 111 such as a blowing fan, a second flow path 112 provided with the second airflow generation device 111 at one end, and a second opening portion 113 which is the other end of the second flow path 112. With the foregoing components, the control airflow generation portion 119 generates a second airflow K2 which is a control airflow. The second airflow K2 controls the odor-containing first airflow K1. The first opening portion 104 is located inside the second opening portion 113. That is, the first opening portion 104 and the second opening portion 113 are provided in such a manner that a movement of the first airflow K1 exiting the first opening portion 104 can be controlled by the second airflow K2.

The first airflow generation device 101 generates an airflow flowing inside the first flow path 102 from the first airflow generation device 101 toward the first opening portion 104. The first airflow generation device 101 may be, for example, an air pump or a blower, and more specifically, a diaphragm pump. The air pump may be a diaphragm pump including a piezoelectric element or a motor.

The first airflow generation device 101 is preferably configured to be able to adjust the flow velocity of the first airflow K1. For example, the first airflow generation device 101 is configured to be able to change the flow velocity of the first airflow K1 stepwise or continuously. This makes it possible to realize more types of odor expression as compared with the case of a device that generates the first airflow K1 having only one flow velocity.

The first flow path 102 has the first airflow generation device 101 connected to one end and is open at the other end, which is the first opening portion 104. The shape of the cross-section (cross-section perpendicular to the axis of the flow path) of the first flow path 102 may be, for example, circular, oval, or rectangular, including square, and may be appropriately selected by a person skilled in the art.

The odor carrying portion 103 imparts an odor to the airflow generated by the first airflow generation device 101. The odor carrying portion 103 may be provided at any position inside the first flow path 102, or, more preferably, is provided so that the airflow generated by the first airflow generation device 101 passes through the odor carrying portion 103.

For example, the odor carrying portion 103 includes an inlet 105 through which the airflow generated by the first airflow generation device 101 enters the odor carrying portion 103, and an outlet 106 through which the airflow passing through the odor carrying portion 103 exits the odor carrying portion 103. An odor can be imparted to the airflow while the airflow entering the odor carrying portion 103 from the inlet 105 passes through the odor carrying portion 103 and exits the outlet 106. More specifically, a volatile gaseous odor component may be included in the airflow. A position at which the odor carrying portion 103 is provided may be, for example, a position closer to the first opening portion 104 in the first flow path 102 than the first airflow generation device 101.

Further, an opening/closing mechanism or a check valve for controlling the passage of an airflow may be provided at the inlet 105 through which the airflow generated by the first airflow generation device 101 enters the odor carrying portion 103. Further, an opening/closing mechanism or a check valve for controlling the passage of an airflow may be provided at the outlet 106 through which the first airflow K1 exits the odor carrying portion 103. Alternatively, an opening/closing mechanism or a check valve for controlling the passage of an airflow may be provided in the first opening portion 104. Thus, an opening/closing mechanism or a check valve for controlling the passage of an airflow may be provided at the inlet 105 through which the airflow generated by the first airflow generation device 101 enters the odor carrying portion 103 and either one of or both of the outlet 106 and the first opening portion 104 through which the first airflow K1 exits the odor carrying portion 103. Odor leakage from the odor carrying portion 103 can be controlled by the opening/closing mechanism or check valve.

The odor carrying portion 103 can contain, for example, a fragrance, and more specifically a liquid fragrance or a solid fragrance. An odor component contained in a fragrance (particularly a liquid fragrance or solid fragrance) is imparted to the airflow generated by the first airflow generation device 101, and the first airflow K1 containing the odor is formed. The liquid fragrance may be included in the odor carrying portion 103 while being impregnated in a fragrance carrier, for example.

The shape of the fragrance carrier may be, for example, spherical, rectangular, triangular, cylindrical, or hollow cylindrical. The material of the fragrance carrier may be, for example, calcium silicate, silica gel, rock wool, diatomaceous earth, zeolite, peat, charcoal, vermiculite, bentonite, perlite, carbon nanotubes, activated carbon, natural fiber (such as cotton or rayon), or felt obtained by processing fibers. The solid fragrance may be a solid substance obtained by solidifying a liquid fragrance using, for example, a gelling agent, or may be a solid material that emits an odor, such as a piece of wood that emits an odor. Further, the odor carrying portion 103 may include a deodorant instead of the liquid fragrance or solid fragrance. The fragrance included in the odor carrying portion 103 may be, for example, a natural fragrance or a synthetic fragrance. The odor carrying portion 103 may include one fragrance or may include a combination of a plurality of fragrances.

Preferably, in the odor presentation module 100, the odor carrying portion 103 may be configured as a cartridge portion 120. For example, the cartridge portion 120 including the odor carrying portion 103 and the first opening portion 104 may be configured to be replaceable. Note that only the odor carrying portion 103 may be configured to be replaceable, and some or all of the odor carrying portion 103, the first opening portion 104, and the first flow path 102 may be replaceable. By making the odor carrying portion 103 replaceable, when odor components contained in the odor carrying portion 103 run out or when the user (user) wishes to change the types of odor components contained in the odor carrying portion 103, the cartridge portion 120 can be replaced, and portions of the odor presentation module 100 other than the cartridge portion 120 can be reused.

The first opening portion 104 can be disposed inside the second opening portion 113, facing in the direction of emission of airflow emission, as shown in FIG. 1. This makes it easy to control the first airflow k1 exiting the first opening portion 104 by the second airflow K2.

The first opening portion 104 is an outlet through which the first airflow K1 containing an odor exits to the outside of the odor presentation module 100. The shape of the opening surface of the first opening portion 104 may be circular, oval, or rectangular (square or rectangular), for example. When the shape of the opening surface of the first opening portion 104 is circular or oval, a diameter or long diameter may be, for example, 0.1 mm to 5 mm, particularly 0.2 mm to 3 mm, more particularly 0.3 mm to 2 mm, and more particularly 0.5 mm to 1.5 mm. When the shape of the opening surface is a square or a rectangle, one side of the square or the long side of the rectangle may be, for example, 0.08 mm to 4 mm, particularly, 0.16 mm to 2.4 mm, more particularly 0.24 mm to 1.6 mm, and more particularly 0.4 mm to 1.2 mm.

With such dimensions, it is possible to operate the first airflow generation device 101 only when necessary, emitting the odor-containing first airflow K1 from the first opening portion 104 to the outside of the odor presentation module 100, and in other cases, it is possible to prevent the odor contained in the odor carrying portion 103 from leaking outside the odor presentation module 100 and reduce fragrance deposition inside the housing.

The cross-sectional dimensions of the first opening portion 104 (especially the dimensions of the shape of the opening surface of the first opening portion 104) may be smaller than the cross-sectional dimensions of the first flow path 102 from the outlet 106 of the odor carrying portion 103 to immediately before the first opening portion 104. For example, the cross-sectional dimensions of the first opening portion 104 and the cross-sectional dimensions of the first flow path 102 from the outlet 106 of the odor carrying portion 103 to immediately before the first opening portion 104 can be set in such a manner that the first airflow K1 is injected from the first opening portion 104. In this manner, the odor presentation module 100 (especially the odor-containing airflow generation portion 109) can be configured such that the odor-containing first airflow K1 is injected from the first opening portion 104.

The first opening portion 104 may be located in front of the second airflow generation device 111 in a traveling direction of the second airflow. For example, the opening surface of the first opening portion 104 may be on the same plane as the opening surface of the second opening portion 113, or may be located in front of the plane in the traveling direction of the second airflow K2. With such arrangement, the odor component contained in the first airflow K1 can be prevented from adhering to a wall surface of the second flow path 112 through which the second airflow K2 flows.

The first airflow K1 emitted from the first opening portion 104 is an airflow containing an odor, and in particular, an airflow containing an odor component included in the odor carrying portion 103. For example, the first airflow K1 may be an airflow of a mixture of the odor component and air in a space in which the odor presentation module is placed. The first airflow K1 emitted from the first opening portion 104 may be, in particular, an airflow formed by injection from the first opening portion 104, and may be, for example, a directional airflow.

As shown in FIG. 1, the first flow path 102 including the odor carrying portion 103 may be provided inside the second flow path 112 provided with the second airflow generation device 111 at one end. This makes it easy to control the first airflow k1 by the second airflow K2. This also makes it easier to present a drifting odor.

The second airflow generation device 111 forms an airflow that flows inside the second flow path 112 in a direction from the second airflow generation device 111 to the second opening portion 113. The second airflow generation device 111 can form the second airflow K2 exiting through the second opening portion 113. The second airflow generation device 111 may be configured to also be able to form an airflow flowing in an opposite direction. That is, the second airflow generation device 111 may be configured to be able to reverse the direction of an airflow to be generated. Thus, the odor presentation module according to the present technology may be configured to change a direction of the second airflow to a direction into the second opening. This makes it possible to collect odor components and enables odor control in the form of odor reduction or elimination.

The second airflow generation device 111 may be, for example, a blower. More specifically, the blower can be an axial fan, a blower fan, and a centrifugal fan, and is particularly an axial fan. For example, the odor presentation module 100 may include an axial fan as the second airflow generation device. Alternatively, the blower may be a combination of a diaphragm pump that uses particularly a piezoelectric element or motor (such as a micro blower) and an airflow expansion mechanism. The blower may be configured such that the airflow generated by the diaphragm pump is expanded by the airflow expansion mechanism and flows through the flow path. For example, the odor presentation module according to the present technology may be a combination of a diaphragm pump and an airflow expansion mechanism, as the second airflow generation device.

Note that, as shown in FIG. 2, the odor presentation module 100 includes four odor-containing airflow generation portions 109. Thus, the odor presentation module 100 may include one odor-containing airflow generation portion 109, or may include a plurality of (for example, two to three, five or more) odor-containing airflow generation portions 109.

The second airflow K2 generated by the second airflow generation device 111 may be an airflow including the air itself in the space in which the odor presentation module 100 is placed, or may be an airflow including air obtained by any other component being mixed with the air in the space. Preferably, the second airflow K2 is the air itself in the space in which the odor presentation module 100 is placed. This makes it easier to control the presentation of the odor of the first airflow K1. For example, the second airflow K2 may be odorless air.

The second airflow generation device 111 is preferably configured to be able to adjust the flow velocity of the second airflow K2. For example, the second airflow generation device 111 is configured to be able to change the flow velocity of the second airflow K2 stepwise or continuously. This makes it possible to realize more types of odor expression as compared with the case of a device that generates the second airflow K2 having only one flow velocity.

The second flow path 112 has the second airflow generation device 111 connected at one end and is open at the other end, which is the second opening portion 113. The shape of the cross-section (cross-section perpendicular to the axis of the flow path) of the second flow path 112 may be, for example, circular, oval, or rectangular (square or rectangular), and may be appropriately selected by a person skilled in the art. The size of the cross-section of the second flow path 112 through which the second airflow K2 flows is preferably larger than the size of the cross-section of the first flow path 102 through which the first airflow K1 flows.

The first flow path 102 through which the first airflow K1 flows is provided inside the second flow path 112 through which the second airflow K2 flows. Thus, the odor presentation module according to the present technology includes a first flow path through which the first airflow flows, and a second flow path through which the second airflow flows, and the first flow path may be provided inside the second flow path.

The second opening portion 113 is an opening portion through which the second airflow K2 formed by the second airflow generation device 111 exits. The area of the opening surface of the second opening portion 113 is preferably larger than the area of the opening surface of the first opening portion 104. For example, the area of the opening surface of the second opening portion 113 may be 3 to 1000 times, particularly 5 to 500 times, and more particularly 10 to 200 times the area of the opening surface of the first opening portion 104. This makes it easier to control the first airflow by the second airflow.

The shape of the opening surface of the second opening portion 113 may be, for example, circular, oval, or rectangular (square or rectangular). If the shape of said opening surface is circular or oval, the diameter or longitudinal diameter may be, for example, 5 mm to 1000 mm, particularly 7 mm to 500 mm, and more particularly 10 mm to 100 mm. If the shape of the opening surface is a square or rectangle, one side of the square or a long side of the rectangle may be, for example, 5 mm to 1000 mm, particularly 7 mm to 500 mm, and more particularly 10 mm to 100 mm.

As shown in FIG. 1, the second airflow generation device 111 may be disposed behind the first opening portion 104 through which the odor-containing first airflow K1 exits (behind a position on an axis of the first opening portion 104 when a traveling direction of the first airflow K1 is taken as the axis).

Alternatively, the second airflow generation device 111 may be located in front of the first opening portion 104. Preferably, as shown in FIG. 1, the second airflow generation device 111 is disposed behind the first opening portion 104 through which the odor-containing first airflow K1 exits. Thus, the odor component contained in the odor-containing first airflow K1 can be prevented from adhering to the second airflow generation device 111 in a case in which the second airflow generation device 111 emits the second airflow K2 from the second opening portion 113.

In the odor presentation module 100 described above, the movement of the first airflow K1 exiting the first opening portion 104 can be controlled by the second airflow K2.

For example, by generating the first airflow K1 while continuously generating the second airflow K2 exiting the second opening portion 113, a drifting odor can be presented to the user, for example. By increasing or reducing the flow rate (air volume) of the second airflow K2, the degree of odor of the first airflow K1 can also be varied. Further, by stopping the generation of the second airflow K2, a localized odor can also be generated by the first airflow K1.

Further, by generating the second airflow K2 entering the odor presentation module from the second opening portion 113, the odor-containing first airflow K1 can be collected. For example, the odor emitted to the outside of the odor presentation module can be collected. As a result, the degree of odor perceived by the user can be weakened, or the user can be prevented from perceiving the odor.

For the odor presentation module 100 shown in FIG. 1, the first opening portion 104 and the second opening portion 113 may be provided on an outer surface of the odor presentation module 100. This allows the first airflow K1 and the second airflow K2 to come into contact with each other outside the odor presentation module 100. Thus, the odor presentation module of the present technology may be configured to allow the first airflow and the second airflow to come into contact with each other outside the odor presentation module.

As described above, the odor presentation module according to the present technology may include, for example, the odor-containing airflow generation portion, and the control airflow generation portion that controls the odor-containing airflow generated by the odor-containing airflow generation portion. The odor-containing airflow generation portion may include a first airflow generation device, an odor component carrying portion through which an airflow generated by the first airflow generation device passes, and a first opening portion through which a first airflow containing an odor formed by passing through the odor component carrying portion exits. The control airflow generation portion can include a second airflow generation device, and a second opening portion through which a second airflow generated by the second airflow generation device exits.

(2) Configuration Example of Retention Nozzle

A configuration example of the retention nozzle 110 applied to the odor presentation module 100 according to the present embodiment will be described next.

The retention nozzle 110 includes a body portion 131 that is detachably mounted on the second opening portion 113 of the control airflow generation portion 119, the body portion being located at a tip of the odor presentation module 100, a curved surface portion 132 that covers the surface of the body portion 131, and a plurality of discharge holes 133 formed on the surface portion 132. An internal space S1 is formed inside the retention nozzle 110, which is surrounded by the body portion 131 and the surface portion 132. The internal space S1 serves as a retention space in which airflow is retained.

The retention nozzle 110 is installed as an obstacle in the path of the first airflow K1 and the second airflow K2 generated from the first airflow generation device 101 and the second airflow generation device 111, to cause retention of these airflows and to diffuse and mix the airflows. Here, if the opening ratio of the discharge holes 133 formed on the surface portion 132 is too large, the airflow retention becomes insufficient to expand the discharge range and reduce the degree of bias reduction of the first airflow K1. If the opening ratio of the discharge holes 133 is too small, a sufficient discharge flow rate cannot be secured. Therefore, it is desired that the opening ratio of the discharge holes 133 be between 1% and 40%, for example.

It is desired that the distance between the first opening portion 104 and the discharge holes 133 be long to some extent. This is because a longer distance reduces the bias of the odor-containing first airflow K1 and also reduces fragrance deposition on the inner surface of the retention nozzle 110. However, if the distance between the first opening portion 104 and the discharge holes 133 is too long, the retention nozzle 110 itself becomes larger, so, for example, between 10 mm and 70 mm is desirable.

As shown in FIG. 1, some of the discharge holes 133 of the retention nozzle 110 are disposed outside the inner diameter of the housing of the odor presentation module 100 by a distance L. This allows the emission range of the discharged airflow emitted from the discharge holes 133 to be larger than the width of the inner diameter of the housing of the odor presentation module 100.

The surface portion 132 of the retention nozzle 110 is formed into a convex shape in an airflow discharge direction, which is upward. This facilitates the widening of the range of airflow to be emitted. Coating the surface portion 132 with a fluorinated resin and/or forming the retention nozzle 110 with fluorinated resin can make it more difficult for fragrances to adhere to the inner surface of the retention nozzle 110.

(3) Operation Example of Odor Presentation Module (Odor Presentation Method)

Next, with reference to FIG. 1 and FIG. 2, an operation example (odor presentation method) in which the odor-containing first airflow K1 is emitted from the odor presentation module 100 will be described.

First, in the odor-containing airflow generation portion 109, an airflow is generated by the first airflow generation device 101. The generated airflow passes through the first flow path 102 and enters the interior of the odor carrying portion 103 from the inlet 105 of the odor carrying portion 103 provided in the first flow path 102. The airflow that has entered the odor carrying portion 103 from the inlet 105 passes through the odor carrying portion 103 and exits through the outlet 106 as the odor-imparted first airflow K1. The first airflow K1 that has exited through the outlet 106 is then emitted from the first opening portion 104 toward the internal space S1 of the retention nozzle 110.

Next, in the control airflow generation portion 119, the second airflow generation device 111 provided at one end of the second flow path 112 generates the second airflow K2, which is the control airflow. The generated second airflow K2 passes through the second flow path 112 and is emitted toward the internal space S1 of the retention nozzle 110 from the second opening portion 113, which is the other end of the second flow path 112. The direction of the first airflow K1 emitted from the first opening portion 104 is controlled by the second airflow K2.

The first airflow K1 emitted from the first opening portion 104 is controlled by the second airflow K2 and at the same time retained temporarily in the internal space S1 of the retention nozzle 110. Then, the retained first airflow K1 is emitted from the discharge holes 133 toward the user to provide a fragrance to the user.

This allows the first airflow K1 to be emitted toward the user after expanding the emission range of the first airflow K1. In addition, when providing a plurality of fragrances to the user, since a plurality of first airflows K1 are mixed in the internal space S1 before being emitted toward the user, it is possible to provide the user with an unbiased fragrance.

In the conventional odor presentation module, the range of the discharged airflow is narrow and must be aimed at the nose of the user with pinpoint accuracy, and when the face of the user moves, the nose moves away from the airflow and loses the smell. However, if the blowing fan of the odor presentation module is enlarged to improve this situation, the odor presentation module becomes larger, making downsizing thereof impossible.

In contrast, according to the odor presentation module 100 of the present embodiment, the first airflow K1 and the second airflow K2 to be emitted toward the user are temporarily retained in the internal space S1 of the retention nozzle 110, which can expand the discharge range of the first airflow K1 and the second airflow K2 and also reduce the bias of the first airflow K1 due to the arrangement of the first opening portion 104. Therefore, according to the odor presentation module 100, a wide range of an odor-containing airflow and a control airflow can be discharged, and downsizing can also be made possible.

2. Second Embodiment

(1) Configuration Example of Odor Presentation Module

Figure 3:
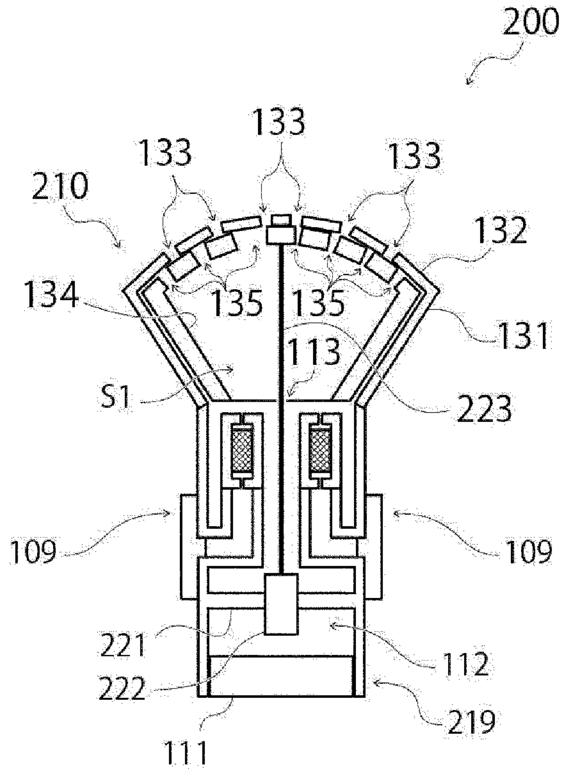
FIG. 3 is a schematic side view showing a configuration example of an odor presentation module according to a second embodiment of the present technology.
Figure 4:
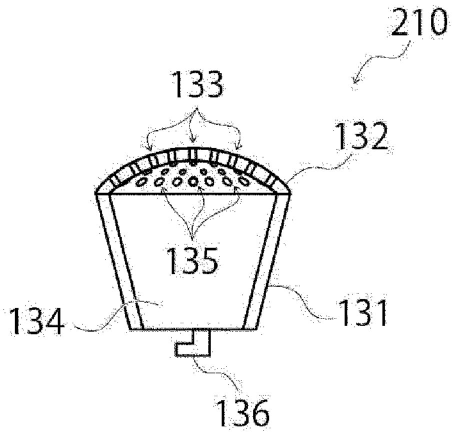
FIG. 4 is a schematic side view showing a configuration example of a retention nozzle according to the second embodiment of the present technology.

Next, a configuration example of an odor presentation module 200 according to a second embodiment of the present technology will be described with reference to FIG. 3 and FIG. 4. FIG. 3 is a schematic side view showing a configuration example of the odor presentation module 200 according to the present embodiment. FIG. 4 is a schematic side view showing a configuration example of a retention nozzle 210 according to the present embodiment.

The odor presentation module 200 differs from the odor presentation module 100 of the first embodiment in being equipped with a shutter mechanism that opens/closes the discharge holes of the retention nozzle. The other configuration of the odor presentation module 200 is similar to that of the odor presentation module 100.

As shown in FIG. 3, the odor presentation module 200 according to the present embodiment includes an odor-containing airflow generation portion 109, a control airflow generation portion 219 that controls an odor-containing airflow generated by the odor-containing airflow generation portion 109, and a retention nozzle 210 that temporarily retains airflows emitted from the odor-containing airflow generation portion 109 and the control airflow generation portion 219.

The retention nozzle 210 includes a body portion 131 that is detachably mounted on the second opening portion 113 of the control airflow generation portion 219, the body portion being located at a tip of the odor presentation module 200, a curved surface portion 132 that covers the surface of the body portion 131, and a plurality of discharge holes 133 formed on the surface portion 132. Inside the retention nozzle 210, the internal space S1 is formed, which is surrounded by the body portion 131 and the surface portion 132.

As shown in FIG. 3 and FIG. 4, the retention nozzle 210 includes an opening/closing mechanism portion 134 that is rotatably inscribed in the body portion 131 and surrounds the internal space S1. The opening/closing mechanism portion 134 is also inscribed in the surface portion 132, and a plurality of inner discharge holes 135 are formed at positions inscribed in the surface portion 132. The retention nozzle 210 further includes an attachment portion 136, such as a hook, to be mounted on the body portion 131.

The desirable optimum conditions for the shape of the retention nozzle 210 are as follows, for example: the diameter of the discharge holes 133 is 2 mm, the pitch interval of each discharge hole 133 is 4.5 mm, the pitch angle of each discharge hole 133 is approximately 60°, the opening ratio of the discharge holes 133 to the entire surface portion 132 is 15%, and the nozzle height from the mounting position of the retention nozzle 210 with respect to the body portion 131 to the topmost position of the surface portion 132 is 35 mm.

Each of the plurality of inner discharge holes 135 is disposed to coincide with each of the plurality of discharge holes 133 when the internal space S1 is open, and is disposed not to overlap each of the plurality of discharge holes 133 when the internal space S1 is closed. Thus, the inner discharge holes 135 function to open and close the discharge holes 133.

In the second flow path 112 of the control airflow generation portion 219, a holding portion 221 is formed to hold a power source that rotates the opening/closing mechanism portion 134. The holding portion 221 holds a rotary motor 222, which is the power source. The rotary motor 222 and the opening/closing mechanism portion 134 are coupled by a rotary shaft 223 extending from the second flow path 112 toward the discharge holes 133. In the present embodiment, the opening/closing mechanism portion 134, the rotary motor 222, and the rotary shaft 223 constitute a shutter mechanism that opens and closes the discharge holes 133.

(2) Operation Example of Shutter Mechanism

Figure 5:
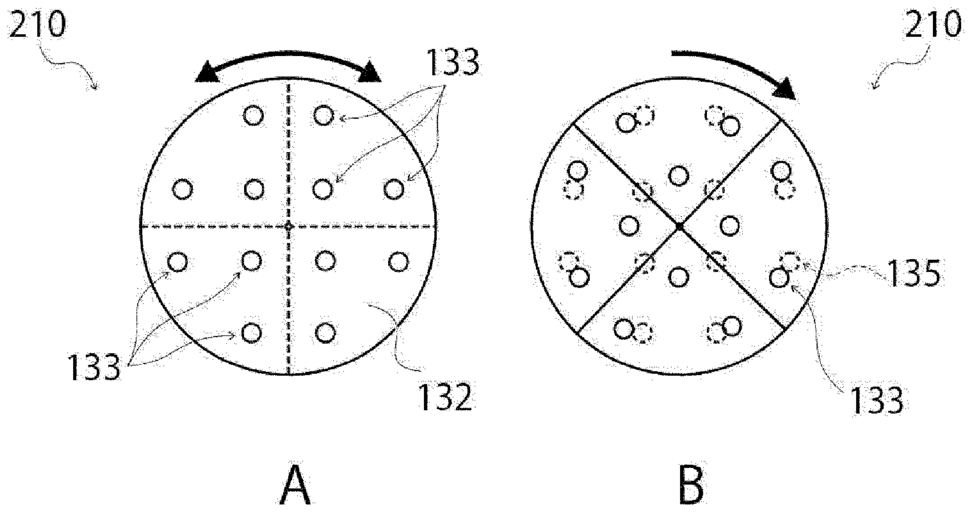
FIG. 5 is a schematic plan view showing an operation example of the retention nozzle according to the second embodiment of the present technology.

Next, with reference to FIG. 5, an operation example of the shutter mechanism that opens and closes the discharge holes 133 of the retention nozzle 210 will be described. FIG. 5A is a schematic plan view of the retention nozzle 210 showing a state in which the discharge holes 133 are open. FIG. 5B is a schematic plan view of the retention nozzle 210 showing a state in which the discharge holes 133 are closed.

As an example, a case in which the shutter mechanism is operated from the state in which the discharge holes 133 of the retention nozzle 210 are open as shown in FIG. 5A to the state in which the discharge holes 133 of the retention nozzle 210 are closed as shown in FIG. 5B will be described.

First, the rotary motor 222 is moved and the rotary shaft 223 coupled to the rotary motor 222 is rotated. Then, since the rotary shaft 223 extends in the front/back direction of the page of FIG. 5A, the opening/closing mechanism portion 134 coupled to the rotary shaft 223 rotates and moves clockwise or counterclockwise in a direction perpendicular to the rotary shaft 223 with respect to the surface portion 132. In the present embodiment, the rotation is clockwise toward the page of FIG. 5A, for example.

As shown in FIG. 5B, this operation causes each inner discharge hole 135 of the opening/closing mechanism portion 134, which was aligned with each discharge hole 133 of the surface portion 132, to shift from the position of each discharge hole 133, and each discharge hole 133 is closed by the opening/closing mechanism portion 134.

In the case of operating the shutter mechanism from the state in which each discharge hole 133 of the retention nozzle 210 is closed to the state in which each discharge hole 133 is opened, each discharge hole 133 can be opened by aligning each discharge hole 133 with each inner discharge hole 135 in the same manner as described above.

According to the odor presentation module 200 of the present embodiment, as with the odor presentation module 100 of the first embodiment, an odor-containing airflow and a control airflow can be discharged over a wide area, and downsizing can also be made possible. Furthermore, according to the odor presentation module 200, since the timing of emitting the odor-containing airflow to the outside can be adjusted, the appropriate concentration (e.g., high concentration) of the odor-containing airflow can be provided to the user after adjusting the mixing concentration, when mixing a plurality of airflows that are retained in the internal space S1.

3. Third Embodiment (1) Configuration Example of Odor Presentation Module

Figure 6:
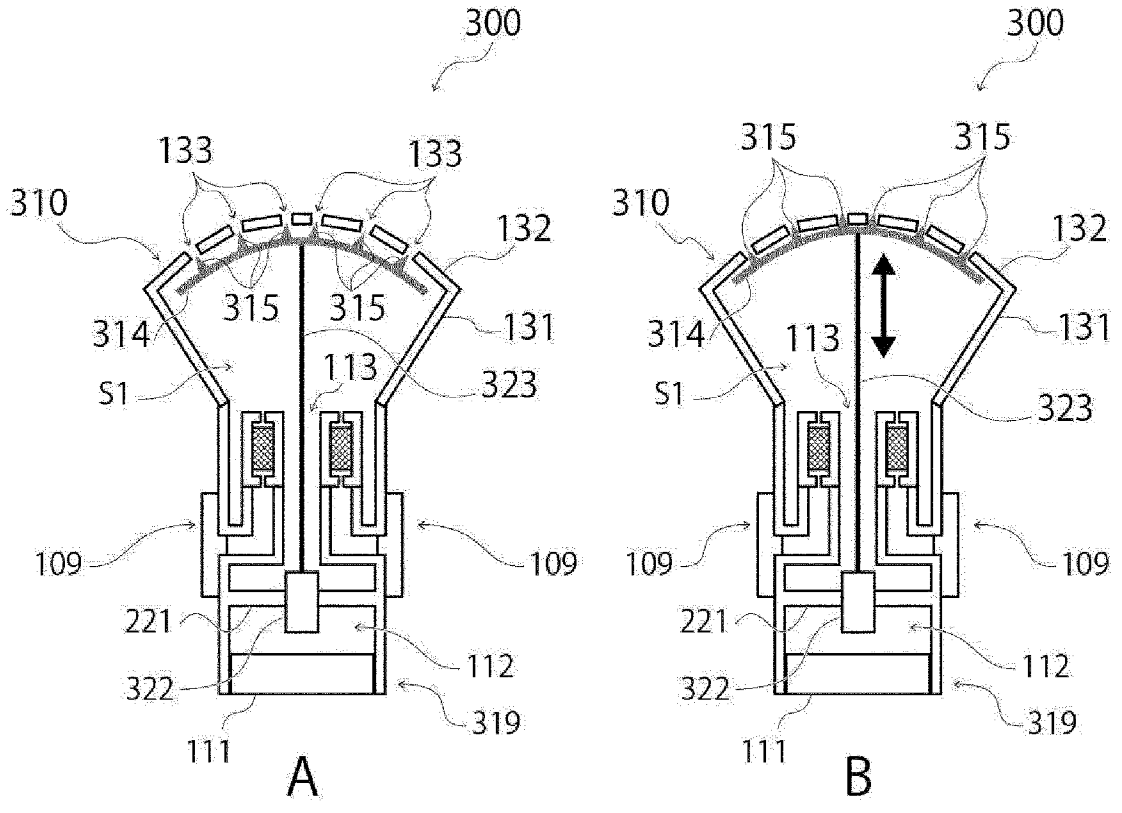
FIG. 6 is a schematic side view showing a configuration example of an odor presentation module according to a third embodiment of the present technology.

Next, with reference to FIG. 6A, a configuration example of an odor presentation module 300 according to a third embodiment of the present technology will be described. FIG. 6A is a schematic side view showing a configuration example of the odor presentation module 300 according to the present embodiment.

The odor presentation module 300 differs from the odor presentation module 200 according to the second embodiment in terms of the structure of the shutter mechanism that opens/closes the discharge holes of the retention nozzle. The other configuration of the odor presentation module 300 is similar to that of the odor presentation module 200.

As shown in FIG. 6A, the odor presentation module 300 according to the present embodiment includes the odor-containing airflow generation portion 109, a control airflow generation portion 319 that controls an odor-containing airflow generated by the odor-containing airflow generation portion 109, and a retention nozzle 310 that temporarily retains airflows emitted from the odor-containing airflow generation portion 109 and the control airflow generation portion 319.

The retention nozzle 310 includes a body portion 131 that is detachably mounted on the second opening portion 113 of the control airflow generation portion 319, the body portion being located at a tip of the odor presentation module 300, a curved surface portion 132 that covers the surface of the body portion 131, and a plurality of discharge holes 133 formed on the surface portion 132. Inside the retention nozzle 310, the internal space S1 is formed, which is surrounded by the body portion 131 and the surface portion 132.

The retention nozzle 310 further includes an opening/closing mechanism portion 314 at a position away from the interior of the surface portion 132. The opening/closing mechanism portion 314 can move to a position in abutment with the interior of the surface portion 132. The opening/closing mechanism portion 314 has a plurality of projections 315 that, when in abutment with the interior of the surface portion 132, are inserted into the respective discharge holes 133 of the surface portion 132.

Each projection 315 is disposed at a position away from each discharge hole 133 when the internal space S1 is open, and is disposed at a position inserted into each discharge hole 133 when the internal space S1 is closed. Thus, the projections 315 function to open and close the discharge holes 133.

In the second flow path 112 of the control airflow generation portion 319, the holding portion 221 is formed to hold a power source that moves the opening/closing mechanism portion 314. A linear actuator 322, which is the power source, is held in the holding portion 221. The linear actuator 322 and the opening/closing mechanism portion 314 are coupled by a coupling shaft 323 extending from the second flow path 112 toward the discharge holes 133. The opening/closing mechanism portion 314 can move in the extension direction in which the coupling shaft 323 extends. In the present embodiment, the opening/closing mechanism portion 314, the linear actuator 322, and the coupling shaft 323 constitute the shutter mechanism that opens and closes the discharge holes 133. The linear actuator 322 can be made of a shape memory alloy (SMA).

(2) Operation Example of Shutter Mechanism

Next, with reference to FIG. 6A and FIG. 6B, an operation example of the shutter mechanism that opens and closes the discharge holes 133 of the retention nozzle 310 will be described. FIG. 6A is a schematic side view of the odor presentation module 300 showing the state in which the discharge holes 133 are open. FIG. 6B is a schematic side view of the odor presentation module 300 showing the state in which the discharge holes 133 are closed.

As an example, a case in which the shutter mechanism is operated from the state in which the discharge holes 133 of the retention nozzle 310 are open as shown in FIG. 6A to the state in which the discharge holes 133 of the retention nozzle 310 are closed as shown in FIG. 6B will be described.

First, the linear actuator 322 is moved, and the coupling shaft 323 coupled to the linear actuator 322 is moved upward in the extension direction. Then, the opening/closing mechanism portion 314 coupled to the coupling shaft 323 also moves until coming into abutment with the surface portion 132, and each projection 315 of the opening/closing mechanism portion 314 is inserted into each discharge hole 133 of the surface portion 132.

As shown in FIG. 6B, this operation closes each discharge hole 133 of the surface portion 132 to be closed by each projection 315 of the opening/closing mechanism portion 134.

In the case of operating the shutter mechanism from the state in which each discharge hole 133 of the retention nozzle 310 is closed to the state in which each discharge hole 133 is opened, each discharge hole 133 can be opened by moving each projection 315 to a position away from each discharge hole 133 in the same manner as described above.

According to the odor presentation module 300 of the present embodiment, as with the odor presentation module 100 of the first embodiment, an odor-containing airflow and a control airflow can be discharged over a wide area, and downsizing can also be made possible. Furthermore, according to the odor presentation module 300, as with the odor presentation module 200 according to the second embodiment, the appropriate concentration of the odor-containing airflow can be provided to the user after adjusting the mixing concentration in the internal space S1 of the retention nozzle 310.

4. Fourth Embodiment (1) Configuration Example of Odor Presentation Module

Figure 7:
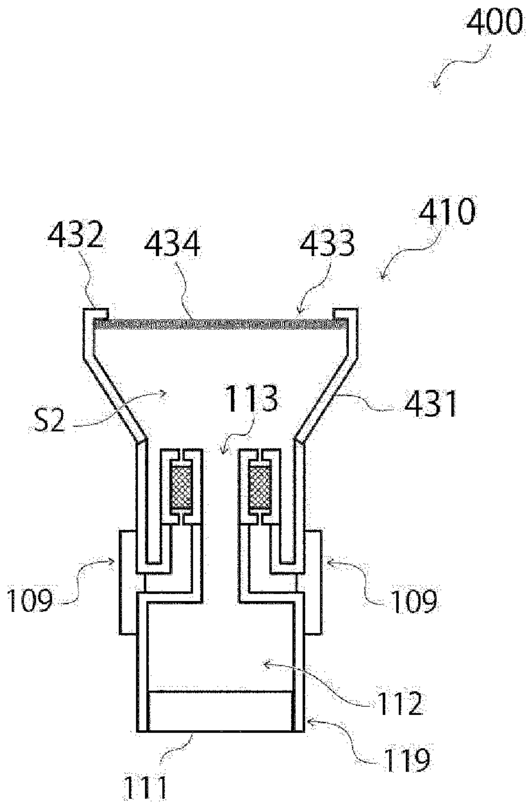
FIG. 7 is a schematic side view showing a configuration example of an odor presentation module according to a fourth embodiment of the present technology.

Next, a configuration example of an odor presentation module 400 according to a fourth embodiment of the present technology will be described with reference to FIG. 7. FIG. 7 is a schematic side view showing a configuration example of the odor presentation module 400 according to the present embodiment.

The odor presentation module 400 differs from the odor presentation module 200 according to the second embodiment in terms of the shape of the retention nozzle and the structure of the shutter mechanism that opens/closes a discharge opening portion. The other configuration of the odor presentation module 400 is similar to that of the odor presentation module 200.

As shown in FIG. 7, the odor presentation module 400 according to the present embodiment includes an odor-containing airflow generation portion 109, a control airflow generation portion 119 that controls an odor-containing airflow generated by the odor-containing airflow generation portion 109, and a retention nozzle 410 that temporarily retains airflows emitted from the odor-containing airflow generation portion 109 and the control airflow generation portion 119.

The retention nozzle 410 includes a body portion 431 that is detachably mounted on the second opening portion 113 of the control airflow generation portion 119, the body portion being located at a tip of the odor presentation module 400, a surface portion 432 of the body portion 431, and a discharge opening portion 433 formed in the center of the surface portion 432. Inside the retention nozzle 410, an internal space S2 is formed, which is surrounded by the body portion 431 and the surface portion 432.

The retention nozzle 410 also includes an opening/closing mechanism portion 434 for opening and closing the discharge opening portion 433 of the surface portion 132. The opening/closing mechanism portion 434 includes a narrowing mechanism 435 that gradually closes the discharge opening portion 433 while narrowing it from an edge of the surface portion 132 toward the center.

The opening/closing mechanism portion 434 stores the narrowing mechanism 435 at the edge of the surface portion 132 when the internal space S2 is open, and the narrowing mechanism 435 closes the discharge opening portion 433 when the internal space S2 is closed. In this manner, the narrowing mechanism 435 functions to open and close the discharge opening portion 433. In the present embodiment, the opening/closing mechanism portion 434 constitutes the shutter mechanism that opens and closes the discharge opening portion 433.

(2) Operation Example of Shutter Mechanism

Figure 8:
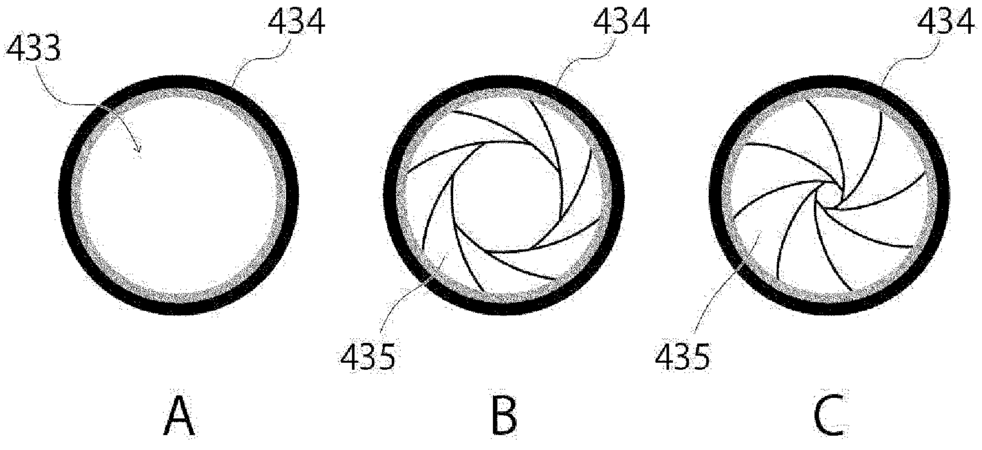
FIG. 8 is a schematic plan view showing an operation example of a retention nozzle according to the fourth embodiment of the present technology.

Next, with reference to FIG. 8A to FIG. 8C, an operation example of the shutter mechanism for opening and closing the discharge opening portion 433 of the retention nozzle 410 will be described. FIG. 8A is a schematic plan view of the opening/closing mechanism portion 434 showing the state in which the discharge opening portion 433 is open. FIG. 8B is a schematic plan view of the opening/closing mechanism portion 434 showing the state in which the discharge opening portion 433 is about to be closed. FIG. 8C is a schematic plan view of the opening/closing mechanism portion 434 showing the state in which the discharge opening portion 433 is closed.

As an example, a case in which the shutter mechanism is operated from the state in which the discharge opening portion 433 of the retention nozzle 410 is open as shown in FIG. 8A to the state in which the discharge opening portion 433 of the retention nozzle 410 is closed as shown in FIG. 8C will be described.

First, in the state in which the discharge opening portion 433 is open as shown in FIG. 8A, the narrowing mechanism 435 of the opening/closing mechanism portion 434 stored at the edge of the surface portion 132 is moved by power transmission from a power source. Then, as shown in FIG. 8B, the narrowing mechanism 435 gradually closes the discharge opening portion 433 while narrowing it from the edge of the surface portion 132 toward the center. As a result of this operation, as shown in FIG. 8C, the discharge opening portion 433 of the surface portion 132 is closed by the narrowing mechanism 435 of the opening/closing mechanism portion 134.

To operate the shutter mechanism from the state in which the discharge opening portion 433 of the retention nozzle 410 is closed to the state in which the discharge opening portion 433 is open, the narrowing mechanism 435 can be stored from the center of the surface portion 132 toward the edge according to the procedure opposite to that described above, thereby opening the discharge opening portion 433.

According to the odor presentation module 400 of the present embodiment, as with the odor presentation module 100 of the first embodiment, an odor-containing airflow and a control airflow can be discharged over a wide area, and downsizing can also be made possible. Furthermore, according to the odor presentation module 400, as with the odor presentation module 200 according to the second embodiment, the appropriate concentration of the odor-containing airflow can be provided to the user after adjusting the mixing concentration in the internal space S2 of the retention nozzle 410.

5. Fifth Embodiment (1) Configuration Example of Odor Presentation Module

Figure 9:
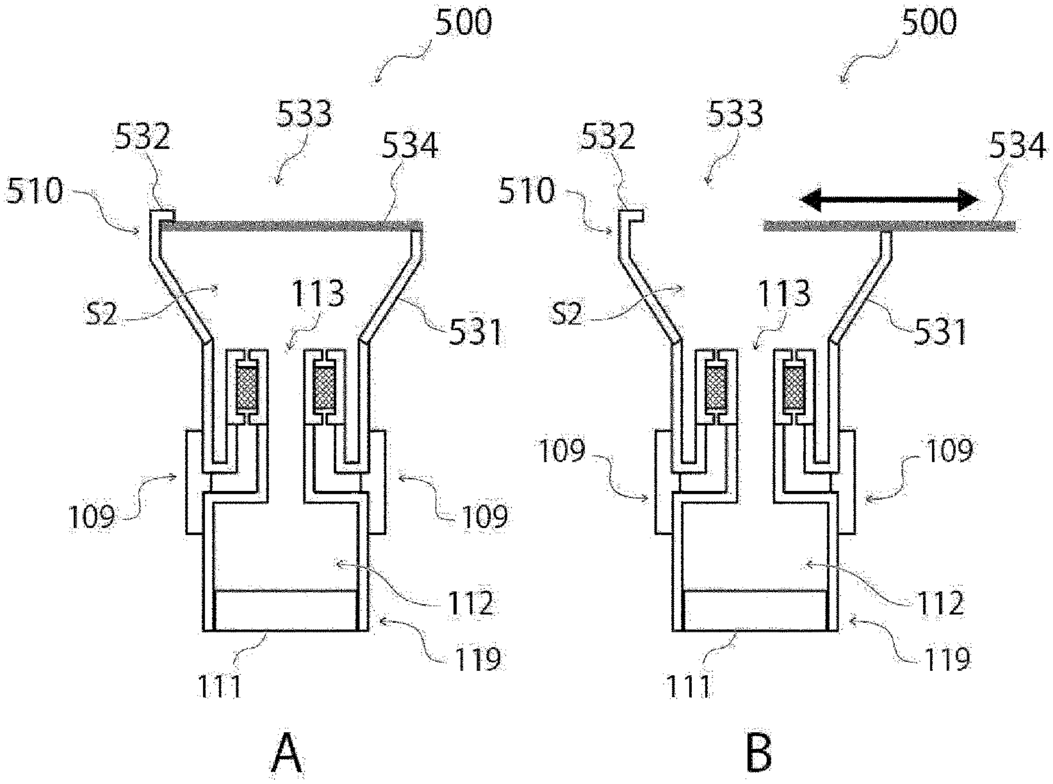
FIG. 9 is a schematic side view showing a configuration example of an odor presentation module according to a fifth embodiment of the present technology.

Next, a configuration example of an odor presentation module 500 according to a fifth embodiment of the present technology will be described with reference to FIG. 9A. FIG. 9A is a schematic side view showing a configuration example of the odor presentation module 500 according to the present embodiment.

The odor presentation module 500 differs from the odor presentation module 400 according to the fourth embodiment in terms of the structure of the shutter mechanism that opens/closes the discharge opening portion. The other configuration of the odor presentation module 500 is similar to that of the odor presentation module 400.

As shown in FIG. 9A, the odor presentation module 500 according to the present embodiment includes the odor-containing airflow generation portion 109, a control airflow generation portion 119 that controls an odor-containing airflow generated by the odor-containing airflow generation portion 109, and a retention nozzle 510 that temporarily retains airflows emitted from the odor-containing airflow generation portion 109 and the control airflow generation portion 119.

The retention nozzle 510 includes a body portion 531 that is detachably mounted on the second opening portion 113 of the control airflow generation portion 119, the body portion being located at a tip of the odor presentation module 500, a surface portion 532 of the body portion 531, and a discharge opening portion 533 formed in the center of the surface portion 532. Inside the retention nozzle 510, the internal space S2 is formed, which is surrounded by the body portion 531 and the surface portion 532.

In the vicinity of the surface portion 532, the retention nozzle 510 further includes an opening/closing mechanism portion 534 for opening and closing the discharge opening portion 533. The opening/closing mechanism portion 534 is disposed so as to be slidable in an opening surface direction of the discharge opening portion 533. In the present embodiment, the opening/closing mechanism portion 534 constitutes the shutter mechanism that opens and closes the discharge opening portion 533.

(2) Operation Example of Shutter Mechanism

Next, with reference to FIG. 9A and FIG. 9B, an operation example of the shutter mechanism for opening and closing the discharge opening portion 533 of the retention nozzle 510 will be described. FIG. 9A is a schematic side view of the odor presentation module 500 showing the state in which the discharge opening portion 533 is closed. FIG. 9B is a schematic side view of the odor presentation module 500 showing the state in which the discharge opening portion 533 is open.

As an example, a case in which the shutter mechanism is operated from the state in which the discharge opening portion 533 of the retention nozzle 510 is closed as shown in FIG. 9A to the state in which the discharge opening portion 533 of the retention nozzle 510 is open as shown in FIG. 9B will be described.

First, in the state in which the discharge opening portion 533 is open as shown in FIG. 9A, the opening/closing mechanism portion 534 located in the vicinity of the surface portion 532 is moved by power transmission from a power source. Then, the opening/closing mechanism portion 534 is caused to slide in the opening surface direction of the discharge opening portion 533 (the right direction toward the page of FIG. 9A), to open the discharge opening portion 533. As a result of this operation, the discharge opening portion 533 of the surface portion 532 is opened by the opening/closing mechanism portion 534, as shown in FIG. 9B.

To operate the shutter mechanism from the state in which the discharge opening portion 533 of the retention nozzle 510 is open to the state in which the discharge opening portion 533 is closed, the discharge opening portion 533 can be closed by sliding the opening/closing mechanism portion 534 in the opening surface direction of the discharge opening portion 533 (the left direction toward the page of FIG. 9B) according to the procedure opposite to that described above.

According to the odor presentation module 500 of the present embodiment, as with the odor presentation module 100 of the first embodiment, an odor-containing airflow and a control airflow can be discharged over a wide area, and downsizing can also be made possible. Furthermore, according to the odor presentation module 500, as with the odor presentation module 400 according to the fourth embodiment, the appropriate concentration of the odor-containing airflow can be provided to the user after adjusting the mixing concentration in the internal space S2 of the retention nozzle 510.

6. Sixth Embodiment (1) Configuration Example of Odor Presentation Module

Figure 10:
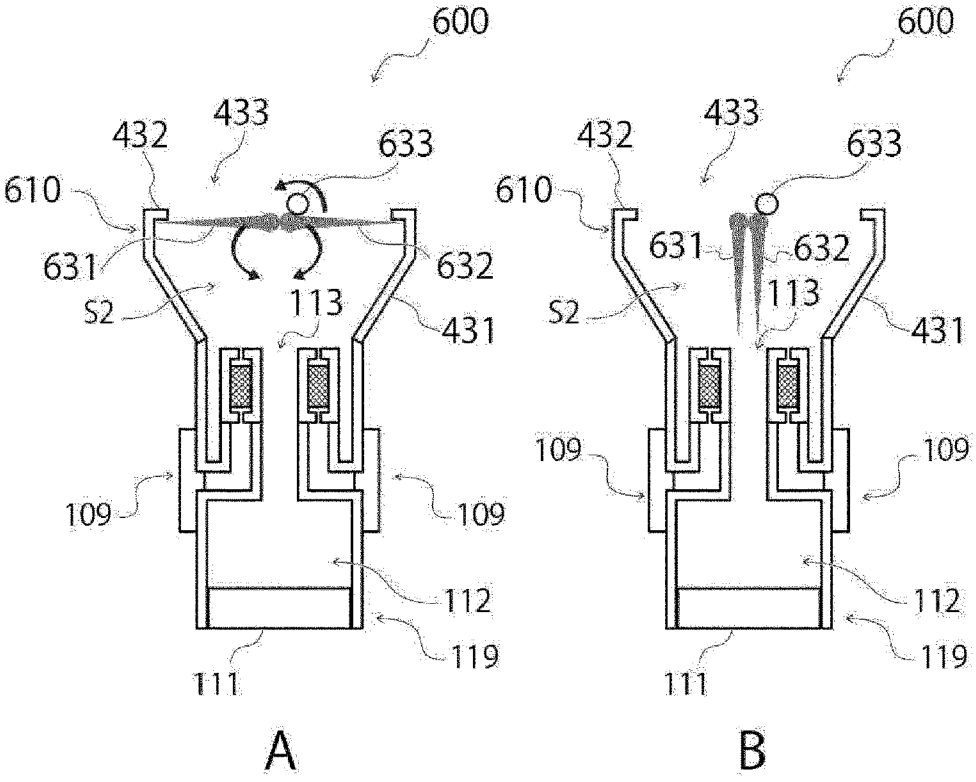
FIG. 10 is a schematic side view showing a configuration example of an odor presentation module according to a sixth embodiment of the present technology.

Next, a configuration example of an odor presentation module 600 according to a sixth embodiment of the present technology will be described with reference to FIG. 10A. FIG. 10A is a schematic side view showing a configuration example of the odor presentation module 600 according to the present embodiment.

The odor presentation module 600 differs from the odor presentation module 400 according to the fourth embodiment in terms of the structure of the shutter mechanism that opens/closes the discharge opening portion. The other configuration of the odor presentation module 600 is similar to that of the odor presentation module 400.

As shown in FIG. 10A, the odor presentation module 600 according to the present embodiment includes the odor-containing airflow generation portion 109, a control airflow generation portion 119 that controls an odor-containing airflow generated by the odor-containing airflow generation portion 109, and a retention nozzle 610 that temporarily retains airflows emitted from the odor-containing airflow generation portion 109 and the control airflow generation portion 119.

The retention nozzle 610 includes a body portion 431 that is detachably mounted on the second opening portion 113 of the control airflow generation portion 119, the body portion being located at a tip of the odor presentation module 600, a surface portion 432 of the body portion 431, and a discharge opening portion 433 formed in the center of the surface portion 432. Inside the retention nozzle 610, the internal space S2 is formed, which is surrounded by the body portion 431 and the surface portion 432.

The retention nozzle 610 also includes an opening/closing mechanism portion 631 and an opening/closing mechanism portion 632 that open and close the discharge opening portion 433 in the center of the surface portion 532. The opening/closing mechanism portion 631 and the opening/closing mechanism portion 632 each have a rotary shaft at the center of the surface portion 532, and rotate around these shafts to open the discharge opening portion 433 by rotating from an opening surface of the discharge opening portion 433 towards the direction of the internal space S2. The retention nozzle 610 further includes a motor rotary shaft 633 as a power source to rotate the opening/closing mechanism portion 631 and the opening/closing mechanism portion 632, the motor rotary shaft 633 being located in the vicinity of the rotary shafts of the opening/closing mechanism portion 631 and the opening/closing mechanism portion 632.

In the present embodiment, the opening/closing mechanism portion 631, the opening/closing mechanism portion 632, and the motor rotary shaft 633 constitute the shutter mechanism for opening and closing the discharge opening portion 433.

(2) Operation Example of Shutter Mechanism

Next, with reference to FIG. 10A and FIG. 10B, an operation example of the shutter mechanism for opening and closing the discharge opening portion 433 of the retention nozzle 610 will be described. FIG. 10A is a schematic side view of the odor presentation module 600 showing the state in which the discharge opening portion 433 is closed. FIG. 10B is a schematic side view of the odor presentation module 600 showing the state in which the discharge opening portion 433 is open.

As an example, a case in which the shutter mechanism is operated from the state in which the discharge opening portion 433 of the retention nozzle 610 is closed as shown in FIG. 10A to the state in which the discharge opening portion 433 of the retention nozzle 610 is open as shown in FIG. 10B will be described.

First, in the closed state of the discharge opening portion 433 as shown in FIG. 10A, the motor rotary shaft 633 is rotary moved. Then, by rotating the motor rotary shaft 633, the rotary shafts of the opening/closing mechanism portion 631 and the opening/closing mechanism portion 632 are rotated. For example, the rotary shaft of the opening/closing mechanism portion 631 is rotated counterclockwise towards the page of FIG. 10A, and the rotary shaft of the opening/closing mechanism portion 632 is rotated clockwise towards the page of FIG. 10A.

Through these operations, as shown in FIG. 10B, the opening/closing mechanism portion 631 and the opening/closing mechanism portion 632 rotate around the respective shafts thereof, from the opening surface of the discharge opening portion 433 towards the direction of the internal space S2, thereby opening the discharge opening portion 433.

To operate the shutter mechanism from the state in which the discharge opening portion 433 of the retention nozzle 610 is open to the state in which the discharge opening portion 433 is closed, the discharge opening portion 433 can be closed by rotating the opening/closing mechanism portion 631 and the opening/closing mechanism portion 632 from the internal space S2 towards the direction of the opening surface of the discharge opening portion 433 according to the procedure opposite to that described above.

According to the odor presentation module 600 of the present embodiment, as with the odor presentation module 100 of the first embodiment, an odor-containing airflow and a control airflow can be discharged over a wide area, and downsizing can also be made possible. Furthermore, according to the odor presentation module 600, as with the odor presentation module 400 according to the fourth embodiment, the appropriate concentration of the odor-containing airflow can be provided to the user after adjusting the mixing concentration in the internal space S2 of the retention nozzle 610.

7. Seventh Embodiment (1) Configuration Example of Odor Presentation Device

Figure 11:
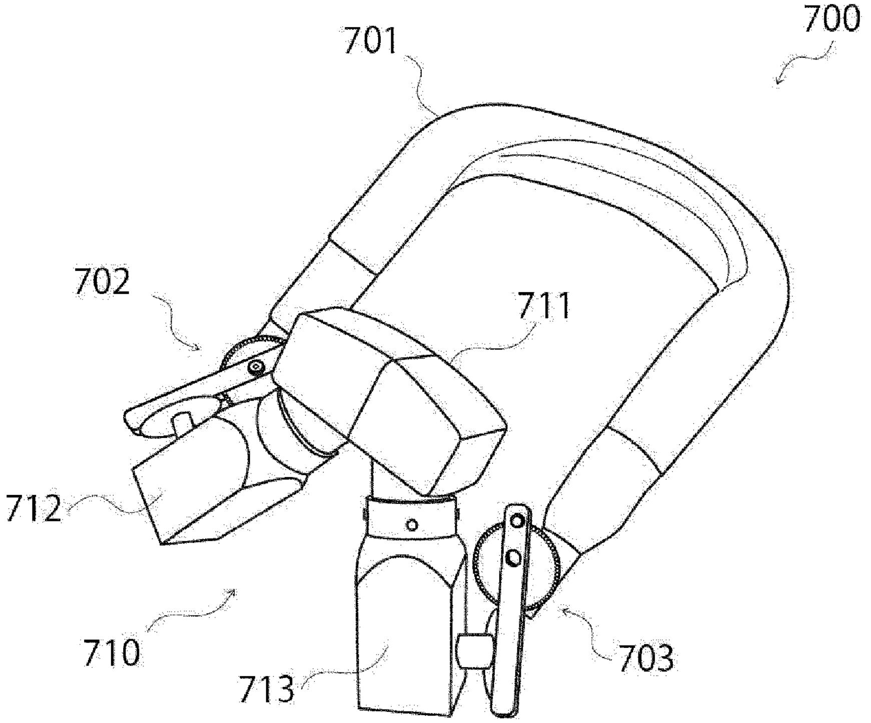
FIG. 11 is a perspective view showing a configuration example of an odor presentation device according to a seventh embodiment of the present technology.

Next, a configuration example of an odor presentation device 700 according to a seventh embodiment of the present technology will be described with reference to FIG. 11. FIG. 11 is a perspective view showing a configuration example of the odor presentation device 700. The odor presentation device 700 is a device having a plurality of odor presentation modules.

As shown in FIG. 11, the odor presentation device 700 according to the present embodiment includes a U-shaped attachment portion 701 worn around the neck or shoulder of the user, an odor presentation portion 710 connected to an end of the attachment portion 701 to present an odor to the user, and a right-side variable mechanism 702 and a left-side variable mechanism 703 that allow for the variation of the position of the odor presentation portion 710 with respect to the attachment portion 701.

The odor presentation portion 710 includes, for example, an odor presentation module 712 connected to an end of the attachment portion 701 through the right-side variable mechanism 702, an odor presentation module 713 connected to an end of the attachment portion 701 through the left-side variable mechanism 703, and a retention nozzle 711 connected to ends of the odor presentation module 712 and the odor presentation module 713 in an airflow emission direction.

(2) Internal Configuration Example of Odor Presentation Portion

Figure 12:
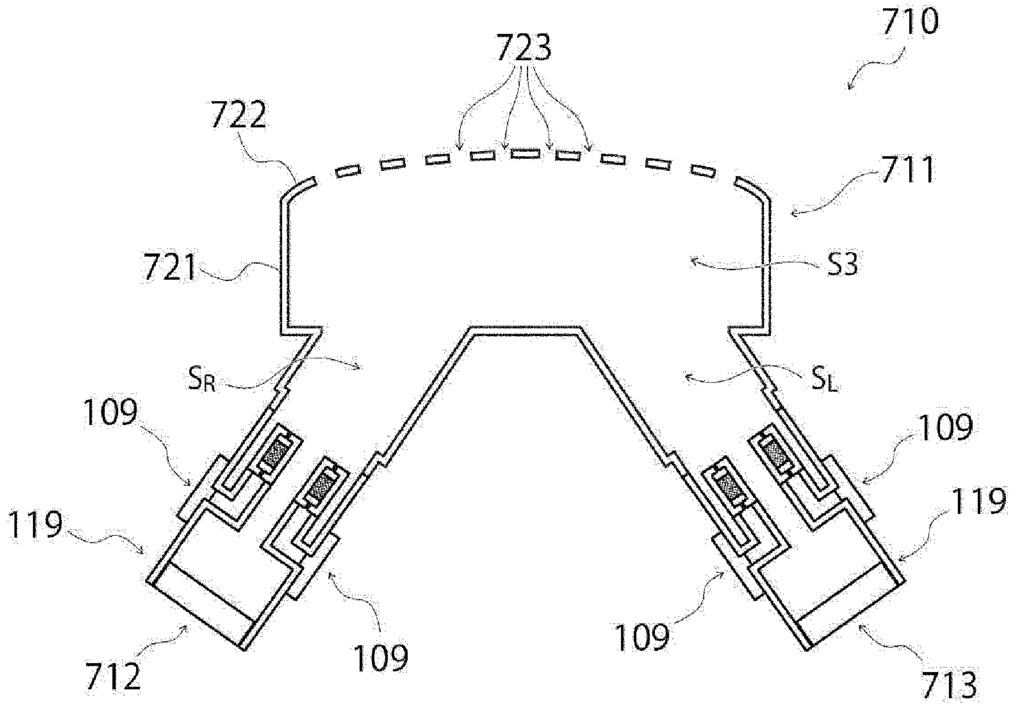
FIG. 12 is an enlarged schematic view showing an internal configuration example of an odor presentation portion according to the seventh embodiment of the present technology.

Next, with reference to FIG. 12, an internal configuration example of the odor presentation portion 710 included in the odor presentation device 700 will be described. FIG. 12 is an enlarged schematic view showing an internal configuration example of the odor presentation portion 710 included in the odor presentation device 700.

As shown in FIG. 12, the odor presentation module 712 and the odor presentation module 713 included in the odor presentation portion 710 each include a plurality of odor-containing airflow generation portions 109 and the control airflow generation portion 119 for controlling an odor-containing airflow generated by the odor-containing airflow generation portions 109.

Additionally, the retention nozzle 711 included in the odor presentation portion 710 includes a body portion 721 that is detachably mounted on tips of the odor presentation module 712 and the odor presentation module 713, a curved convex surface portion 722 that covers the surface of the body portion 721, and a plurality of discharge holes 723 formed on the surface portion 722.

Inside the retention nozzle 711, an internal space S3 is formed, which is surrounded by the body portion 721 and the surface portion 722. Also inside the retention nozzle 711, an internal space $S_R$ for directing an airflow emitted from the odor presentation module 712 towards an internal space S3, and an internal space $S_L$ for directing an airflow emitted from the odor presentation module 713 towards the internal space S3 are formed. In the internal space S3, a plurality of airflows flowing in from the internal spaces $S_R$ and the internal space $S_L$ can be integrated.

Between the body portion 721 and the odor presentation modules 712 and 713, there is provided a rotating mechanism that allows forward and backward movement of the retention nozzle 711. A variable mechanism 702 and a variable mechanism 703 with 3-axis rotation and alignment mechanisms for changing the position of the retention nozzle 711 are connected to the respective ends of the odor presentation module 712 and the odor presentation module 713.

The retention nozzle 711 is formed in such a manner that the intersection point of the centerlines of the odor presentation module 712 and the odor presentation module 713 enter the internal space S3. The retention nozzle 711 is also formed to be divided into left and right parts for ease of attachment to the user and can be coupled during use and divided after use.

It is desirable that the distance between the opening portions from which the airflows of the odor presentation module 712 and the odor presentation module 713 are emitted and the discharge holes 723 be somewhat long. This is to reduce the bias in the odor-containing first airflow K1 and to reduce the fragrance deposition on the inner surface of the retention nozzle 711. However, if the distance between the opening portion and the discharge holes 723 is too long, the retention nozzle 711 itself becomes too large; thus, 10 mm to 100 mm, for example, is desirable.

(3) Configuration Example of Variable Mechanism

Figure 13:
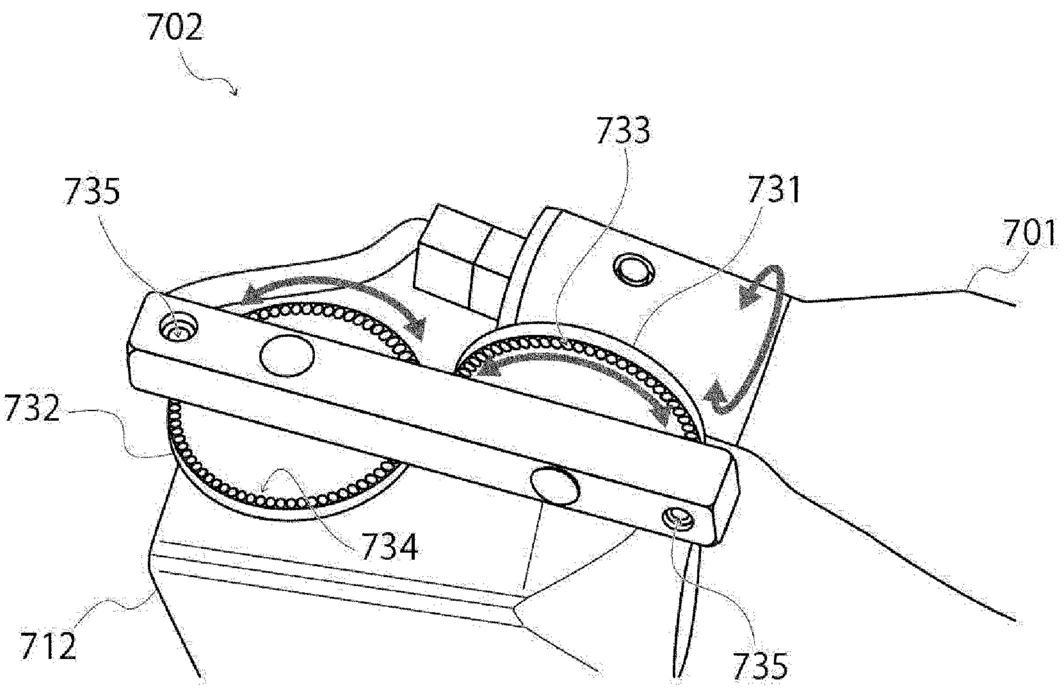
FIG. 13 is an enlarged schematic view showing a configuration example of a variable mechanism according to the seventh embodiment of the present technology.
Figure 14:
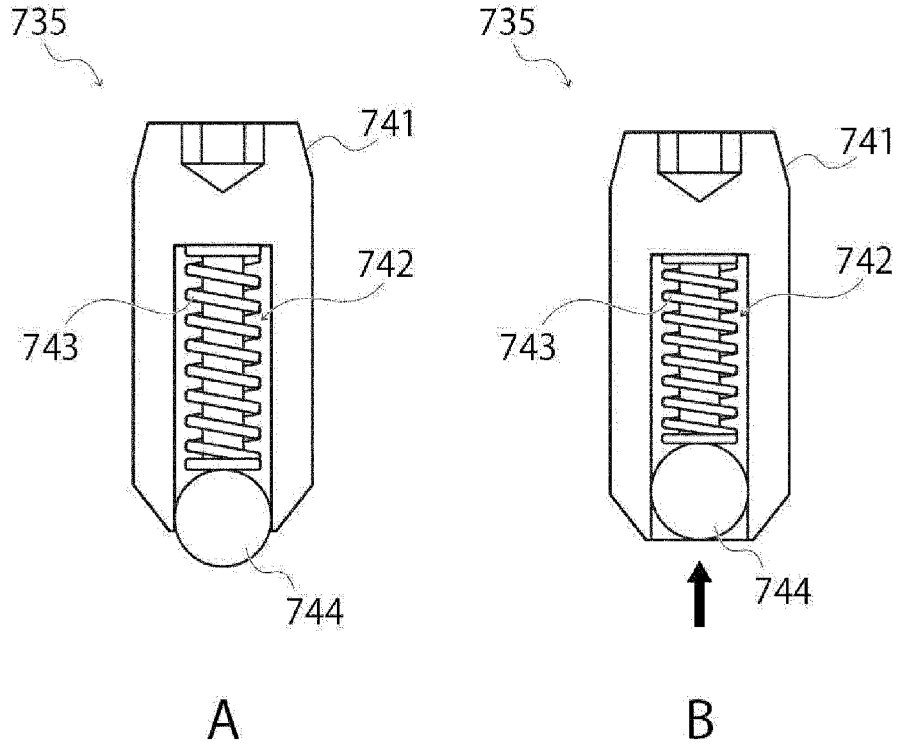
FIG. 14 is a schematic view showing a configuration example of a ball plunger of the variable mechanism according to the seventh embodiment of the present technology.

Next, with reference to FIG. 13 and FIG. 14, configuration examples of the variable mechanisms included in the odor presentation device 700 will be described. FIG. 13 is an enlarged schematic view showing a configuration example of the right-side variable mechanism 702 included in the odor presentation device 700. FIG. 14A is a schematic view showing a configuration example of a ball plunger of the right-side variable mechanism 702. FIG. 14B is a schematic view showing the state in which a ball portion of the ball plunger of the right-side variable mechanism 702 is accommodated inside.

As shown in FIG. 13, the right-side variable mechanism 702 includes a rotary plate 731 connected to an end of the attachment portion 701, and a rotary plate 732 connected to an end of the odor presentation module 712. A plurality of groove portions 733 and groove portions 734 are formed on the circumferences of the surfaces of the rotary plate 731 and the rotary plate 732, respectively.

As shown in FIG. 14A, the ball plunger 735 includes a plunger body portion 741, a spacer 742, a spring 743, and ball portions 744.

When adjusting the position of the odor presentation portion 710, first, as shown in FIG. 14B, the ball portions 744 of the ball plunger 735 are accommodated inside the plunger body portion 741, and in this state the rotary plate 731 and the rotary plate 732 are rotated. After determining the position of the odor presentation portion 710 and stopping the rotation of the rotary plate 731 and the rotary plate 732 at that position, as shown in FIG. 14A, the ball portions 744 are caused to protrude from the plunger body portion 741 by the spring 743, and the ball portions 744 are hooked and fixed to the groove portions 733 and the groove portions 734.

In an example of using a plurality of odor presentation modules, a method of attaching them to left and right ends of a neckband to be worn around the neck is considered. By attaching the plurality of odor presentation modules to the left and right ends of the neckband, it becomes easy to hang them around the neck, and the more odor presentation modules, the more scents can be handled.

However, when the plurality of odor presentation modules are used, there is a problem that does not arise in single use: the airflows from the left and right odor presentation modules do not mix. In this case, a fragrance gas emitted from the right nostril can only be delivered to the right nostril and not to the left nostril. Since humans undergo a nasal cycle in which the dominant nostril or the left and right sensitivity changes with time, an odor to only one nostril results in a variation in the perception of the odor.

In contrast, according to the odor presentation device 700 of the present embodiment, the provision of the above-described configuration can expand the discharge range of an odor-containing airflow and a control airflow, and reduces the bias of the odor-containing airflow due to the arrangement of the opening portions from which the airflows of the odor presentation module 712 and the odor presentation module 713 are emitted. Therefore, according to the odor presentation device 700, a wide range of odor-containing airflow and control airflow can be discharged, and downsizing can also be made possible.

The odor presentation device 700 also has the effect of reducing the bias of the odor-containing airflow due to the arrangement of the odor presentation module, making it easier to deliver the fragrance to both nostrils (reducing the influence of the dominant nostril and the nasal cycle), reducing the impact of the position of the nose even if it moves, and eliminating the need for detailed settings even if the physique and the like vary.

In addition, the odor presentation device 700 can be easily hung around the neck of the user because the retention nozzle 711 can be divided into left and right parts. Furthermore, since the odor presentation device 700 is provided with the right side variable mechanism 702 and the left-side variable mechanism 703, the retention nozzle 711 can be moved back and forth or changed at a fixed angle while worn around the neck of the user.

The present technology can be configured as follows.

(1)

An odor presentation module, comprising:

a first opening portion that emits a first airflow containing an odor;

a second opening portion that emits a second airflow; and a retention nozzle having a retention space in which the first airflow and the second airflow are retained, wherein a direction of the first airflow emitted from the first opening portion is controlled by the second airflow.

(2)

The odor presentation module according to (1), wherein the retention nozzle can be attached to and detached from the second opening portion.

(3)

The odor presentation module according to (1) or (2), wherein the retention nozzle has a plurality of discharge holes.

(4)

The odor presentation module according to any one of (1) to (3), further comprising a first airflow generation device and an odor carrying portion that carries the odor, wherein the first airflow is formed by mixing an airflow generated by the first airflow generation device and the odor carried by the odor carrying portion.

(5)

The odor presentation module according to any one of (1) to (4), further comprising a second airflow generation device that generates the second airflow.

(6)

The odor presentation module according to (5), wherein the first opening portion is located in front of the second airflow generation device in a traveling direction of the second airflow.

(7)

The odor presentation module according to any one of (1) to (6), wherein the first opening portion is formed into a shape for injecting the first airflow.

(8)

The odor presentation module according to any one of (1) to (7), wherein a width of the retention space of the retention nozzle is greater than a width of the second opening portion.

(9)

The odor presentation module according to any one of (1) to (8), wherein the retention nozzle is formed into a convex shape in an airflow discharge direction.

(10)

The odor presentation module according to any one of (1) to (9), wherein a surface of the retention nozzle is coated with a fluorinated resin and/or the retention nozzle is formed of a fluorinated resin.

(11)

The odor presentation module according to any one of (1) to (10), wherein the retention nozzle is provided with a shutter mechanism for opening and closing the discharge holes of the retention nozzle.

(12)

An odor presentation device, comprising:

a plurality of odor presentation modules having a first opening portion for emitting a first airflow containing an odor and second opening portions for emitting a second airflow, a direction of the first airflow emitted from the first opening portion being controlled by the second airflow; and a retention nozzle that has a retention space in which the first airflow and the second airflow emitted from the plurality of odor presentation modules are integrated and retained, and that can be attached to and detached from each of the second opening portions.

(13)

The odor presentation device according to (12), wherein a rotating mechanism is provided at a junction between the retention nozzle and each of the odor presentation modules.

(14)

The odor presentation device according to (12), further comprising an alignment mechanism that allows each of the odor presentation modules to rotate in three axial directions.

(15)

An odor presentation method, comprising the steps of:
- emitting a first airflow containing an odor;
- emitting a second airflow; and
- retaining the first airflow and the second airflow in a retention space,
- wherein a direction of the first airflow that is emitted is controlled by the second airflow.

REFERENCE SIGNS LIST

100, 200, 300, 400, 500, 600, 712, 713 Odor presentation module
101 First airflow generation device
102 First flow path
103 Odor carrying portion
104 First opening portion
105 Inlet
106 Outlet
109 Odor-containing airflow generation portion
110, 210, 310, 410, 510, 610, 711 Retention nozzle
111 Second airflow generation device
112 Second flow path
113 Second opening portion
119, 219, 319 Control airflow generation portion
120 Cartridge portion
131, 431, 531, 721 Body portion
132, 432, 532, 722 Surface portion
133, 723 Discharge hole
134, 314, 434, 534, 631, 632 Opening/closing mechanism portion
135 Inner discharge hole
136 Attachment portion
221 Holding portion
222, 322 Power source
223, 633 Rotary shaft
315 Projection
323 Coupling shaft
433, 533 Discharge opening portion
435 Narrowing mechanism
700 Odor presentation device
701 Attachment portion
702, 703 Variable mechanism
710 Odor presentation portion
731, 732 Rotary plate
733, 734 Groove portion
735 Ball plunger
741 Plunger body portion
742 Spacer
743 Spring
744 Ball portion
K1, K2 Airflow
S1, S2, S3, $S_R$, $S_L$ Internal space

The invention claimed is:

1. An odor presentation device, comprising:
- a plurality of odor presentation modules having a first opening portion for emitting a first airflow containing an odor and second opening portions for emitting a second airflow;
- a direction of the first airflow emitted from the first opening portion being controlled by the second airflow;
- a retention nozzle that has a retention space in which the first airflow and the second airflow emitted from the plurality of odor presentation modules are integrated and retained, and that can be attached to and detached from each of the second opening portions, and
- a rotating mechanism is provided at a junction between the retention nozzle and each of the odor presentation modules.

2. The odor presentation device according to claim 1, wherein the retention nozzle has a plurality of discharge holes.

3. The odor presentation device according to claim 1, wherein the first opening portion is formed into a shape for injecting the first airflow.

4. The odor presentation device according to claim 1, wherein a width of the retention space of the retention nozzle is greater than a width of the second opening portion.

5. The odor presentation device according to claim 1, wherein the retention nozzle is formed into a convex shape in an airflow discharge direction.

6. The odor presentation device according to claim 1, wherein one or both of a surface of the retention nozzle is coated with a fluorinated resin and the retention nozzle is formed of a fluorinated resin.

7. The odor presentation device according to claim 1, wherein the retention nozzle is provided with a shutter mechanism for opening and closing discharge holes of the retention nozzle.

8. An odor presentation device, comprising:
- a plurality of odor presentation modules having a first opening portion for emitting a first airflow containing an odor and second opening portions for emitting a second airflow;
- a direction of the first airflow emitted from the first opening portion being controlled by the second airflow;

a retention nozzle that has a retention space in which the first airflow and the second airflow emitted from the plurality of odor presentation modules are integrated and retained, and that can be attached to and detached from each of the second opening portions; and an alignment mechanism that allows each of the odor presentation modules to rotate in three axial directions.

9. The odor presentation device according to claim 8, wherein the retention nozzle has a plurality of discharge holes.

10. The odor presentation device according to claim 8, wherein the first opening portion is formed into a shape for injecting the first airflow.

11. The odor presentation device according to claim 8, wherein a width of the retention space of the retention nozzle is greater than a width of the second opening portion.

12. The odor presentation device according to claim 8, wherein the retention nozzle is formed into a convex shape in an airflow discharge direction.

13. The odor presentation device according to claim 8, wherein one or both of a surface of the retention nozzle is coated with a fluorinated resin and the retention nozzle is formed of a fluorinated resin.

14. The odor presentation module according to claim 8, wherein the retention nozzle is provided with a shutter mechanism for opening and closing discharge holes of the retention nozzle.

* * * * *